United States Patent
Ritzer et al.

(10) Patent No.: US 8,336,372 B2
(45) Date of Patent: Dec. 25, 2012

(54) METHOD TO DETERMINE THE CONCENTRATION OF TONER PARTICLES FOR A LIQUID DEVELOPER SYSTEM

(75) Inventors: Alfons Ritzer, Dorfen (DE); Werner Zollner, Eitting (DE)

(73) Assignee: Océ Printing Systems GmbH, Poing (DE)

(*) Notice: Subject to any disclaimer, the term of this patent is extended or adjusted under 35 U.S.C. 154(b) by 209 days.

(21) Appl. No.: 12/558,687

(22) Filed: Sep. 14, 2009

(65) Prior Publication Data

US 2011/0058838 A1  Mar. 10, 2011

(30) Foreign Application Priority Data

Sep. 15, 2008 (DE) .................. 10 2008 047 196

(51) Int. Cl.
*G01N 15/06* (2006.01)
(52) U.S. Cl. .................................. 73/61.75
(58) Field of Classification Search .............. None
See application file for complete search history.

(56) References Cited

U.S. PATENT DOCUMENTS

| | | | |
|---|---|---|---|
| 4,825,116 A | 4/1989 | Itoh et al. | |
| 5,121,629 A | 6/1992 | Alba | |
| 6,263,171 B1 | 7/2001 | Oyamada | |
| 6,497,140 B1 | 12/2002 | Zeqiri | |
| 6,959,589 B1 | 11/2005 | Soong et al. | |
| 2007/0283748 A1 | 12/2007 | Funck et al. | |
| 2007/0286626 A1* | 12/2007 | Du et al. | 399/57 |

FOREIGN PATENT DOCUMENTS

| | | |
|---|---|---|
| DE | 38 15 359 A1 | 11/1988 |
| DE | 199 44 047 A1 | 4/2001 |
| DE | 100 45 847 Br | 6/2001 |
| DE | 10 2007 025 251 A1 | 12/2007 |
| EP | 1 850 125 A1 | 10/2007 |
| JP | 3-153278 | 1/1991 |
| JP | 10-268645 | 9/1998 |
| JP | 2000-146825 | 5/2000 |
| JP | 2001-42652 | 2/2001 |
| JP | 2003-186309 | 7/2003 |
| WO | WO 2006/021266 A1 | 3/2006 |

OTHER PUBLICATIONS

Application Note 1041. Understanding Integrating ADCs. Maxim inc. May 2, 2002.*
Accuracy in Real Time Ultrasonic Applications and Transit-Time Flow Meters—Halit Eren 1998 (IEEE)—pp. 568-572.

* cited by examiner

*Primary Examiner* — Hezron E Williams
*Assistant Examiner* — Mark A Shabman
(74) *Attorney, Agent, or Firm* — Schiff Hardin LLP (57) ABSTRACT

In a method to determine concentration of toner particles in a carrier fluid in a liquid developer system for a printer or carrier, a suspension of the carrier fluid in the toner particles is charged with an ultrasonic wave. A propagation time of the ultrasonic wave in the suspension is determined. A concentration of the toner particles in the suspension is determined from the propagation time. A system is also provided employing the above steps.

10 Claims, 6 Drawing Sheets

Toner: Cyan

METHOD TO DETERMINE THE CONCENTRATION OF TONER PARTICLES FOR A LIQUID DEVELOPER SYSTEM

BACKGROUND

The preferred embodiment concerns a method to determine the concentration of toner particles in a carrier fluid in a liquid developer system for printers or copiers. The invention also concerns a measurement chamber to determine the concentration of toner particles in a carrier fluid.

In printers and copiers, a liquid developer system which contains a suspension made up of carrier fluid and toner particles is frequently used to ink a latent image on an intermediate carrier. These toner particles then gave the image the necessary color, for example black, monochrome or color mixtures. The concentration of toner particles in the carrier fluid fluctuates depending on different environmental conditions, for example depending on the evaporation of the carrier fluid as a result of temperature fluctuations and/or humidity fluctuations, and in particular depending on the proportion of ink per printed page. This concentration of toner particles can consequently be higher or lower than a desired operating value. Without countermeasures, a change of the concentration produces a variation of the fluidity of the liquid developer, and therefore a variation of its ability to be processed. Moreover, the mobility of the electrically charged toner particles which are exposed to an external electrical field can vary, whereby the quality of the inking of the latent image on the intermediate carrier is negatively affected. Moreover, the inking of the latent image is dependent on the concentration of the toner particles. It is therefore necessary to keep the current concentration of toner particles at a constant optimal operating value over the operating time during the operation of the printer or copier. For this a regulation process is generally used, wherein it is necessary to continually establish the concentration of toner particles in the carrier fluid.

From Patent Abstracts of Japan JP 03146356 A it is known to keep the concentration of toner particles uniformly constant during the coating process. For this a detector detects the electrical resistance between two electrodes that are submerged in the suspension of carrier fluid and toner particles.

A liquid developer method in which toner particles jump over onto charged paper and thereby mask the paper charge is known from Patent Abstracts of Japan JP 03153278 A. After the development, the paper charge is a measure of the completeness of the development process, and indirectly a measurement for the toner concentration.

A measurement method to measure the toner concentration in which a toner image on the photoconductor is subjected to an optical reflection measurement is known from Patent Abstracts of Japan JP 10268645 A. The concentration of the toner is concluded from the measurement result. A similar method is also described in JP 11065295 A.

From Patent Abstracts of Japan JP 2000146827 A and JP 2001042652 A it is known to determine the concentration of toner particles with the aid of an optical sensor that evaluates the transmission.

From Patent Abstracts of Japan JP 2003186309 A it is known for a liquid developer system to determine the toner concentration via reflection measurement with the aid of an optical reflex sensor.

From U.S. Pat. No. 5,121,629 A it is known to determine the concentration of particles in a suspension with the aid of an ultrasound sensor. Ultrasound waves with selected, discrete frequencies across a selected frequency range are directed towards the suspension, and the attenuation of the amplitudes of the ultrasound waves upon penetration of the suspension are measured.

A method and a device in which ultrasound sensors are used to measure the concentration of solid particles in a suspension is known from DE 199 44 047 C2. Ultrasound waves are conducted through the suspension on at least two different sound paths. The absorption of ultrasound in the suspension is determined, and the concentration of the particles is determined from this.

A method to determine drinking water consumption by means of ultrasonic measurement is known from WO 2006/021266 A1. A measurement signal is thereby emitted that is derived from a clock signal. A capacitor is charged after the received signal has exceeded a reference value after a wait time and a rising edge of the clock signal appears. The charging of the capacitor is ended as soon as a rising edge of the output signal appears. The charge time together with the wait time yields the total measurement time. The water consumption is determined from the measurement time. The method is applied to a clear liquid in which the attenuation of the received oscillation is comparably low.

A measurement chamber to measure a solid concentration by means of ultrasound is known from DE 10 2007 025 251 A1. An emitter emits an ultrasonic wave at an emulsion of carrier fluid and toner particles. The emulsion is thereby pumped through the measurement chamber. The receiver receives the ultrasonic wave. The measurement chamber is thereby arranged horizontally so that the fluid flows through the measurement chamber in the horizontal direction. If the fluid does not flow, solid particles can deposit on the floor (and thus on the receiver), whereby the measurement result is adulterated.

Optical detection methods have the disadvantage that they are imprecise given strongly absorbent carrier fluids. Moreover, gas bubbles in the suspension can significantly adulterate the measurement. Electrical sensors that evaluate the conductivity of the suspension to determine the concentration are likewise relatively imprecise since the conductivity properties can change significantly during the operation of the printer or copier. Moreover, toner particles can adhere to the electrodes, which adulterates the measurement result.

SUMMARY

It is an object to specify a method to determine the concentration of toner particles for a liquid developer system that determines the concentration with high precision during the operation, is simple to implement and is less prone to disruption.

In a method to determine concentration of toner particles in a carrier fluid in a liquid developer system for a printer or carrier, a suspension of the carrier fluid in the toner particles is charged with an ultrasonic wave. A propagation time of the ultrasonic wave in the suspension is determined. A concentration of the toner particles in the suspension is determined from the propagation time. A system is also provided employing the above steps.

DESCRIPTION OF THE PREFERRED EMBODIMENT

For the purposes of promoting an understanding of the principles of the invention, reference will now be made to the preferred embodiment/best mode illustrated in the drawings and specific language will be used to describe the same. It will nevertheless be understood that no limitation of the scope of the invention is thereby intended, and such alterations and further modifications in the illustrated device and such further applications of the principles of the invention as illustrated as would normally occur to one skilled in the art to which the invention relates are included.

According to the preferred embodiment, the suspension of carrier fluid and toner particles which represents the liquid developer is charged with at least one ultrasonic wave. The preferred embodiment proceeds from the consideration that the speed of sound of the sound propagating in the suspension depends essentially on the proportion of toner particles in the carrier fluid within predetermined temperature limits and concentration limits and given consistent carrier fluid. The propagation time of the ultrasonic wave along a predetermined measurement distance in the suspension is accordingly a measure of the speed of sound. The concentration of the toner particles in the suspension can thus be determined from the propagation time.

The propagation time measurement results in a short period of time, such that a high measurement sequence is possible and the method is suitable for online determination of the concentration. The measured propagation time is independent of the optical absorption degree of the carrier fluid and the toner particles. The method can thus be used for a plurality of carrier fluids and toners or toner mixtures. Furthermore, the method is insensitive to gas bubbles contained in the suspension. No mechanically moving parts are required for measurement, such that the method can be simple to design and use. Furthermore, the method is independent of changes of the optical properties or the conductivity properties of the suspension during the operation of the printer or copier. The concentration value can be directly determined in % by volume or % by weight via calibration. An indirect electrical variable such as voltage or current can also be used as a measure of the propagation time.

In the preferred embodiment, the measurement of the propagation time occurs with the aid of a microprocessor via a combined system made up of: coarse digital detection of a wait time within which the ultrasonic wave propagates in the measurement cell but cannot arrive at the receiver; and the generation of a high-resolution, analog voltage via charging of a capacitor in order to precisely determine the remaining delay until the arrival of the ultrasonic wave. The capacitor voltage is in turn digitally evaluated by the microprocessor via the ND converter as a digital value with high resolution.

The temperature of the suspension is advantageously determined. The concentration of the toner particles is then determined from the propagation time and the measured temperature. It is known that the speed of sound is also dependent to a significant degree on the temperature of the suspension. The precision with which the concentration of the toner particles is determined can be increased by taking this temperature into account.

The connection between the propagation time of the ultrasonic wave, the concentration of the toner particles, the carrier fluid and the temperature of the suspension is determined in calibration procedures, wherein known carrier fluids and known concentration values of toner particles are used for this. Because the corresponding function has been determined as a characteristic line or table, in the running operation of the printer or copier the concentration value present in the suspension can be determined from the determined propagation time of the sound wave (possibly via interpolation) and under consideration of the current temperature from the stored characteristic lines and/or tables in the running operation of the printer or copier.

According to a further aspect of the preferred embodiment, a measurement chamber is specified that is advantageously used to implement the method.

For a better understanding of the present invention, in the following reference is made to the preferred exemplary embodiment shown in the drawings, which preferred exemplary embodiment is described using specific terminology. However, it is noted that the protective scope of the invention should not thereby be limited, since such variations and additional modifications to the shown devices and/or the methods and such further applications of the invention as they are indicated therein are viewed as typical present or future knowledge of a competent man skilled in the art. The Figures show an exemplary embodiment of the invention.

Figure 1:
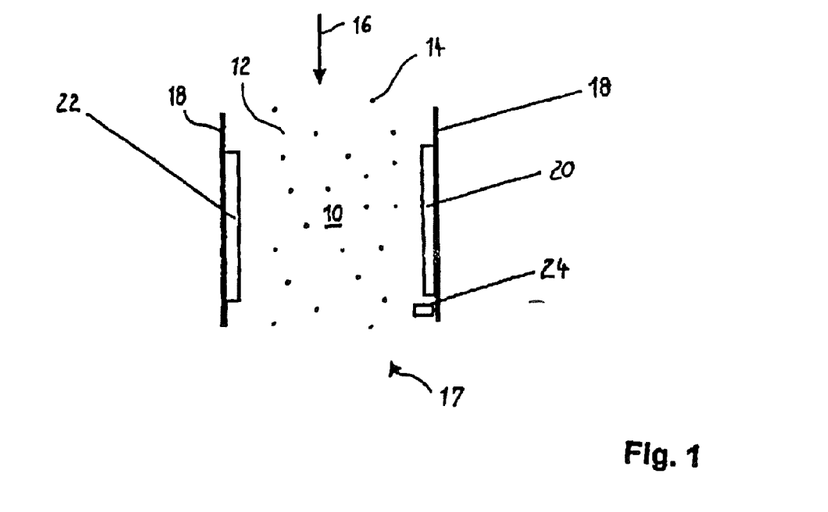
FIG. 1 is a schematic measurement arrangement to determine the propagation time of sound waves in a suspension.

FIG. 1 schematically shows the design of a measurement arrangement to determine the propagation time of ultrasonic waves in a suspension 10 that contains carrier fluid 12 and toner particles 14. The suspension 10 flows in the direction of the arrow 16 through a measurement chamber 17 whose walls 18 are schematically represented. The suspension 10 is extracted from a fluid circuit of an electrographic printer or copier (not shown) and supplied to the measurement chamber 17. Alternatively, the measurement chamber 17 is completely switched into the fluid circuit for the liquid developer system.

An ultrasonic emitter 20 and an ultrasonic receiver 22 are arranged on opposite sides in the measurement chamber 17 along with a temperature sensor 24. Ultrasonic emitters and/or ultrasonic receivers are preferably used in the film form, for example PVDF films (polyvinylidene fluoride films). Similar films are advantageously used for the ultrasonic emitters and the ultrasonic receivers. The film form has the advantage that emitters and/or receivers in the measurement chamber are easy to clean. Moreover, the thickness change of the film is optimally coupled into the suspension due to the relatively large emitting surface. Other piezoelectric materials whose wave resistance is adapted to that of the suspension 10 (in particular to that of the carrier fluid 12) can likewise be used.

For example, silicone oil or another typical developer carrier fluid is considered as a carrier fluid 12. Black toner or color toner with the primary colors magenta, yellow and cyan are considered as toner particles. Other colors (for example in the forms of customer-specific colors) are also possible. In many colors the characteristic lines for the toner particles are approximately identical in broad ranges of the speed of sound, meaning that a common characteristic line set or a calculation formula can be used for the concentration determination for many different colors/carrier fluids.

The speed of sound for a typical carrier fluid is in the range from 800 m/s to 2000 m/s. The delay resulting between ultrasonic emitter 20 and ultrasonic receiver 22 for an ultrasonic wave is dependent on the distance between emitter and receiver. The smaller the distance that is selected, the more precisely that the propagation time measurement must be conducted in order to be able to determine this propagation time with a sufficient precision, and therefore the concentration of toner particles. The distance between ultrasonic emitter 20 and ultrasonic receiver 22 is typically in the centimeter range, in particular one to two centimeters. Typical propagation times of $t_L=21.46$ μs result from this given a speed of sound of 932 m/s, and $t_L=18.18$ μs given a speed of sound of 1100 m/s and a distance of 2 cm.

Figure 2:
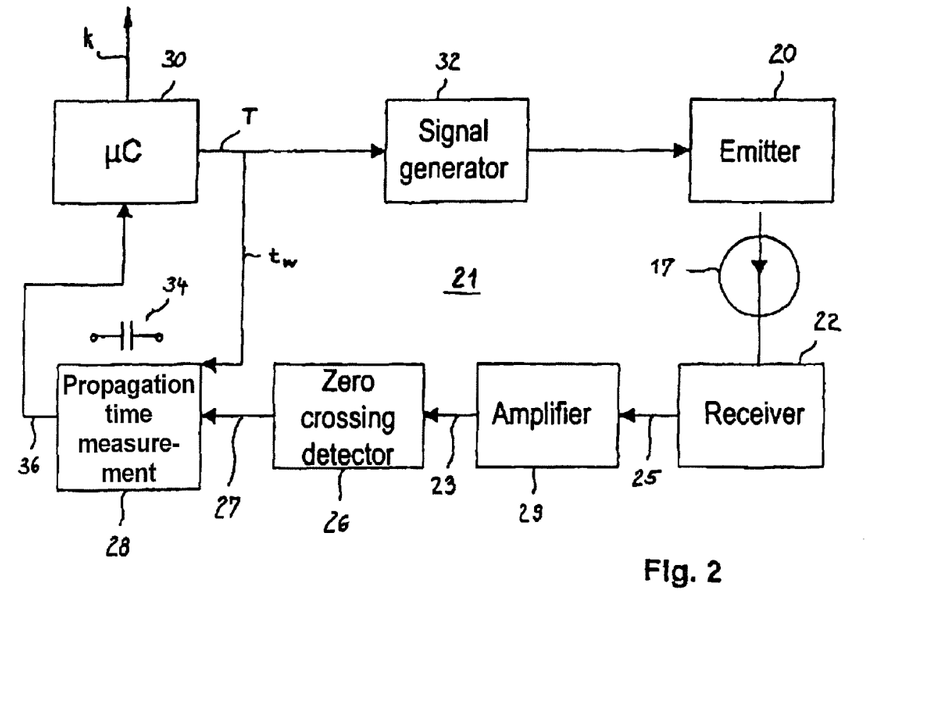
FIG. 2 a block diagram of the hardware configuration to determine the toner concentration.

FIG. 2 shows a measurement device 21 to measure the propagation time of the ultrasonic waves in the measurement chamber 17. A microcomputer 30 takes over the control to determine the propagation time. It sends a start signal to a signal generation device 32 that prepares a power signal for the ultrasonic emitter 20. With the aid of this signal generation device 32, the ultrasonic emitter 20 emits one or more sound waves. Only a single complete oscillation train is advantageously emitted. The sound wave permeates the measurement chamber 17 and, after a propagation time $t_L$, strikes the ultrasonic receiver 22, which generates an electrical receiver signal 25. This receiver signal 25 is amplified with the aid of an amplifier 29 into a signal 23 and is supplied to a zero crossing detector 26. The zero crossing detector 26 generates a signal 27 when a first zero crossing of the oscillation curve of the amplified signal 23 is present after reaching a first maximum or a first minimum. For this, a specific threshold for the maximum or minimum must be reached in order to activate the zero crossing detector. If the threshold is not reached, the detector for the zero crossing is deactivated. Previously received interference signals (for example due to the pulse excitation or external influences) of the receiver are thereby effectively suppressed and prevent incorrect measurements.

The signal 27 controls the propagation time measurement device 28. This propagation time measurement device 28 is started by the microcomputer 30 at the earliest after the expiration of a wait time $t_w$ after the signal to generate an ultrasonic wave has been started. At the point in time $t_w$ the zero crossing detector 26 is also no longer blocked. The propagation time measurement device 28 contains as a significant element a capacitor 34 that is charged as of a start point in time until the signal 27 emitted by the zero crossing detector 26 ends the charging. The voltage 36 present at the capacitor 34 is converted by an A/D converter (for example a 10-bit A/D converter) contained in the propagation time measurement device 28 into a digital value that is supplied to the microcomputer 30 that calculates the total propagation time of the ultrasonic wave in the suspension 10 and determines the concentration value k from this. The A/D converter can advantageously be integrated into the microcomputer 30.

In its memory the microcomputer 30 contains tables or characteristic lines or a toner-dependent calculation formula that was determined in calibration processes. Tables, characteristic lines and formulas can naturally also be held in an external, superordinate controller to which the propagation time measurement values are supplied, and the toner concentration is determined from these. This variant can be used given frequently changing colors and in printers with multiple printing groups. In a calibration process, the function $k=f(t_L, \theta)$ is determined for known carrier fluids with known concentration values k-space and known temperature values θ. In this equation, $t_L$ is the propagation time of the ultrasonic wave in the suspension 10. Such characteristic lines or tables are determined for a plurality of carrier fluids and a plurality of toner particles in multiple calibration processes. In running operation of the printer or copier, the present concentration value k of the toner particle concentration in the suspension 10 is determined from the propagation time $t_L$ (possibly via interpolation) and the temperature value θ.

The distance between emitter and receiver changes in a temperature-dependent manner due to the temperature expansion of the measurement cell. The signal propagation time thereby changes, and is dependent both on the properties of the cells that are used and on those of the fluid that is used. In order to also be able to use the function $k=f(t_L, \theta)$ for measurement chambers that are not structurally identical, the propagation time change that is caused by the temperature expansion of the measurement chamber must be compensated. For this the propagation times $t_N$ are measured at different temperatures for a calibration fluid in every measurement cell M, the temperature-dependent speed of sound $v_K(\theta)$ of which calibration fluid is known (for example for distilled water). The measurement cell-dependent function $t_M(\theta)$ is thereby obtained, and thus also the temperature-dependent distance between emitter and receiver: $d_{S-E-M}(\theta)=v_K(\theta)*t_M(\theta)$. The speed of sound $v_L$ of a measurement fluid can therefore be determined independent of the temperature expansion of the cell via calculation of $v_L=t_M(\theta)/d_{S-E-M}(\theta)$. The function $k=f(v_L, \theta)$ is then used in the following.

Alternatively, the temperature-dependent delay $t_b, K_1(\theta)$ of an arbitrary fluid in a specific chamber can be measured. The temperature-dependent delay $t_{n,K2}(\theta)$ is then obtained via measurement of the same fluid in a second chamber. The propagation times of both chambers at a specific temperature can therefore be converted into one another.

Figure 3:
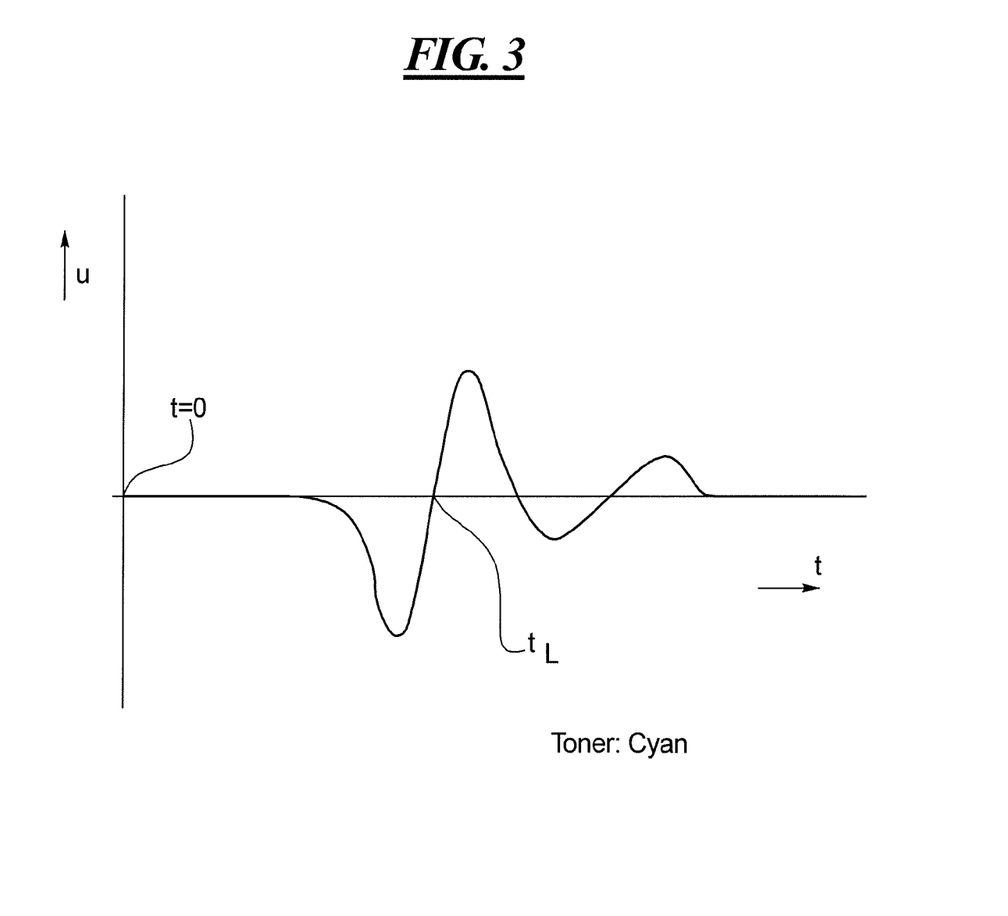
FIG. 3 shows the electrical signal emitted by an ultrasound receiver over time t, and its evaluation.

FIG. 3 shows an example for the determination of the propagation time $t_L$ of the ultrasonic wave in the measurement chamber 17 given toner particles of the color cyan. The received and amplified signal 23 has a similar curve in other colors. The voltage U of the signal 23 of the amplifier 29 is plotted over the time t. At the point in time t=0, the microcomputer 30 outputs the start signal to the signal generator 32, whereupon the ultrasonic emitter 20 emits its single ultrasonic wave. The ultrasonic wave passes through the suspension 10 in the measurement chamber 17 and reaches the ultrasonic receiver 22. Before the arrival of the ultrasonic wave, the signal 23 of the amplifier 29 is equal to zero. The ultrasonic receiver 22 generates a negative voltage U due to the piezo-effect. After crossing a minimum, this voltage again reaches the value of zero. The zero crossing detector 26 detects this zero crossing at the point in time $t_L$ and emits its signal 27 to the propagation time measurement device 28, which stops the charging of the capacitor 34. The evaluation of the zero crossing has the advantage that this zero crossing is independent of the level of the signal amplitude, and thus the attenuation of the sound wave in the suspension remains unconsidered. The evaluation with the aid of a charging of the capacitor 34 is advantageous because the integration process that thereby occurs is less prone to disruption, and its analog voltage 36 can be resolved very well (for example with the aid of an A/D converter contained in the microcomputer 30 or the propagation time measurement device 28). The evaluation of the capacitor charge 36 does not need to occur immediately after the stop of the charging process but rather can also occur at a later point in time, for example after a few 100 μs.

Possible trailing echoes of the ultrasonic wave in the fluid, or charge preparations for the generation of a new sound wave and the interference signals that are caused by these, can be reduced by waiting. The capacitor charge is kept constant in the meanwhile.

The signal curve shown in FIG. 3 is typically charged with an offset voltage so that the shown zero line actually lies at a bias voltage of approximately 2.5 V. The comparators and amplifiers are operated with an asymmetrical operating voltage; at 2.5 V, the working point corresponds to half of the operating voltage. The switching threshold for the detection of the required minimum or maximum value of the received signal is below 2.5 V; the switching threshold for the zero crossing detection is at 2.5 V. The crossing of the signal curve at 2.5 V then corresponds to the zero crossing shown in FIG. 3 at the point in time $t_L$.

The preferred embodiment is implemented using a microprocessor from whose digital clock signal T (derived from the oscillation frequency of a quartz-controlled oscillating circuit) the start signal for the emission of the ultrasonic wave and the starting of the loading process is in turn derived. This clock signal T has a clock interval $\Delta t$ which, due to the typically used clock-controlled clock generator, has a high repetition precision and a low temperature response. It is now advantageous to begin the charging of the capacitor 34 at the earliest after a predetermined wait time $t_w$. The time span within which the receipt of the ultrasonic wave is signaled is then smaller, with the consequence that within this time span the charge voltage can be better resolved given a correspondingly steep voltage rise and a subsequent analog-digital conversion. The voltage of the capacitor 34 is converted by an A/D converter whose digital value corresponds to a charge time tc. The run time $t_L$ to be determined (which is a measure for the concentration of the toner particles in the suspension 10) is then calculated from the sum of wait time $t_w$ and charge time tc. If the wait time $t_w$ is an integer multiple of the clock interval $\Delta t$, this wait time is very precise due to the quartz-controlled clock generation and is also subject to a slight temperature response. Since both values (namely wait time $t_w$ and voltage at the charged capacitor 34) exist as digital values, the evaluation with the aid of the microprocessor is relatively simple, wherein a high precision is nevertheless achieved. This high precision of the propagation time measurement makes it possible to use a small measurement chamber 17 so that the application of the described method leads to a simple hardware design and a compact style.

In practice, propagation time measurements with a resolution <ns across multiple minutes could be implemented with the aid of the described method. The electronic components are typically selected so that the voltage at the capacitor reaches the maximum ND converter voltage within 4 clock intervals $\Delta T$ after the start of the charging, wherein a sufficient resolution is achieved with a 10-bit A/D converter.

Figure 4:
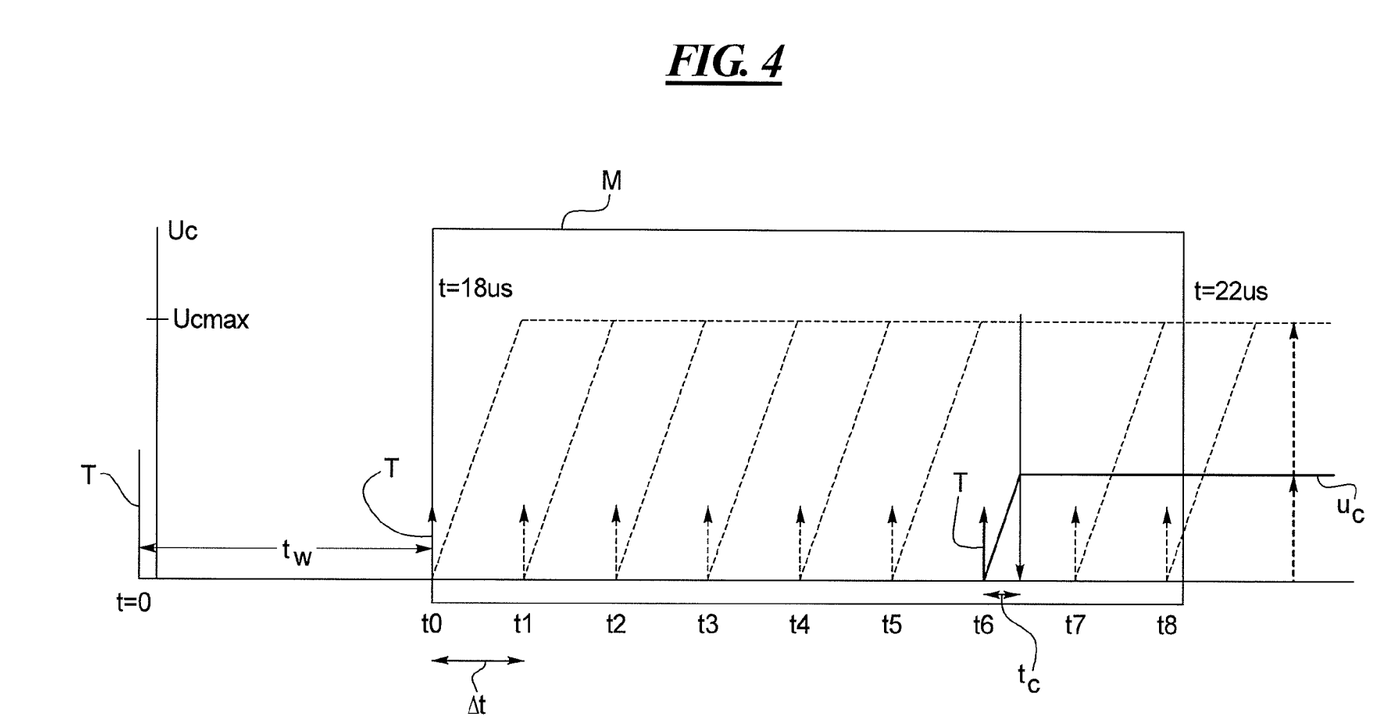
FIG. 4 is an exemplary embodiment in which a measurement region is scanned.

FIG. 4 shows an additional variant of the measurement method. In this variant an optimal point in time at which the loading of the capacitor 34 is started is determined with the aid of the microprocessor. It is hereby assumed that the slope of the charge curve at the capacitor 34 is set such that its maximum voltage is achieved shortly after the passage of a clock interval $\Delta t$, meaning that the maximum charge time tc is slightly larger than the clock interval $\Delta t$. Given an input voltage range of the A/D converter that is adapted to this, the method then operates with maximum resolution. Given a flatter charge curve, the method operates the same but with reduced resolution. After passage of the wait time $t_w$, the first discharged capacitor 34 is charged at the beginning of a new measurement cycle at the point in time t0 of a first clock pulse T within a clock interval $\Delta t$. If the receipt of an ultrasonic wave is not signaled by the ultrasonic receiver 22 within this associated clock interval $\Delta t$, the capacitor 34 is discharged again and a new measurement cycle begins in which this capacitor 34 is charged at the point in time t1 of the next clock pulse T within the following clock interval $\Delta t$.

As is apparent using FIG. 4, the time shift of the beginning of the charge of the capacitor 34 by a respective clock interval $\Delta t$ occurs until the ultrasonic receiver 22 signals the receipt of the ultrasonic wave for the first time at the point in time t6 of the seventh clock pulse T within the following clock interval $\Delta t$ after passage of the charge time tc. The associated voltage value $U_c$ is a measure of the charge time tc. After A/D conversion (for example with the aid of a 10-bit converter), the charge time tc exists as a digital value. The propagation time $t_L$ thus results according to the following relation:

$$t_L = t_w + n \times \Delta t + tc,$$

wherein n is the number of clock intervals $\Delta t$ after passage of the wait time $t_w$.

FIG. 4 shows the measurement range M scanned with the aid of the microprocessor, which measurement range M runs from a time t=18 µs to t=22 µs, for example. This measurement range M can be varied depending on the carrier fluid of the suspension that is used or further parameters. From the absence of the receipt of an ultrasonic wave within a clock interval $\Delta t$ it is recognized that the voltage at the capacitor 34 exceeded a predetermined maximum value Ucmax.

If the scanning of the measurement range M in the search for the receipt of an ultrasonic pulse proceeds without any result, meaning that no zero crossing of a received signal is detected within the established measurement range M, the measurement cycle is started from the beginning at t0. The absence of a zero crossing can exist when, for example, the measurement chamber 17 contains no fluid or the speed of sound lies outside of a predetermined range. Given a fruitlessly repeated scanning of the measurement range M, this can be increased or shifted within the scope of a software routine in order to adapt it to the current speed of sound or carrier fluid.

An additional increase in precision results when the slope m in V/s of the charge curve with which the capacitor 34 is charged within a clock interval $\Delta t$ is set so that the voltage at the end of the clock interval $\Delta t$ is slightly smaller than the maximum input voltage range of the A/D converter. In this case, a maximum resolution of the digital value (and therefore a maximum time resolution of the clock interval $\Delta t$) are achieved.

Figure 5:
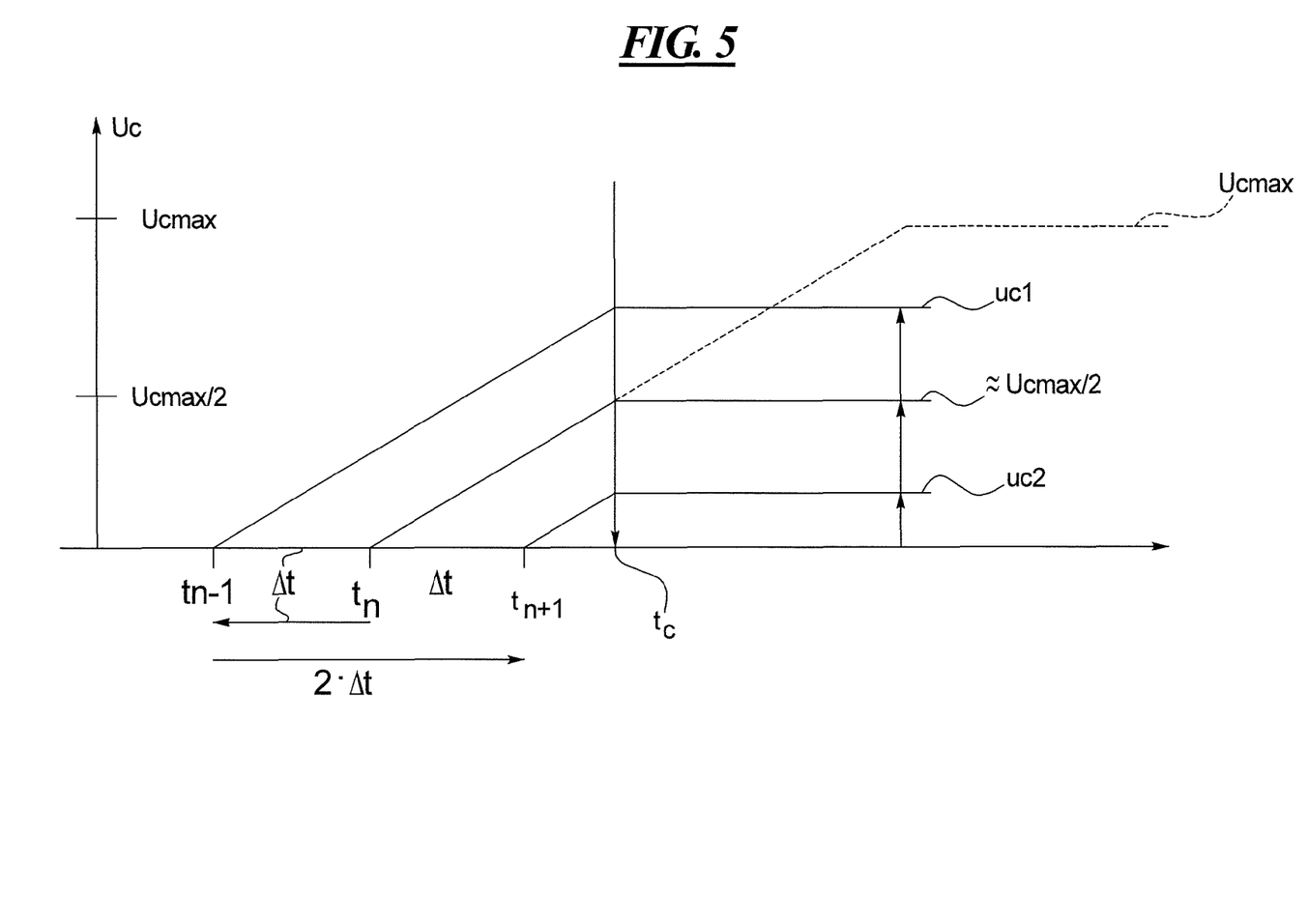
FIG. 5 is an example to determine the slope m of the capacitor charge curve at the working point.

FIG. 5 shows an additional variant in which the slope m of the charge curve is determined around the working point in on-line operation. The precision can be additionally increased in this way. An optimization of the voltage range occurs in a first step. It is thereby necessary that the maximum A/D converter voltage is only reached after the charging across multiple time intervals $\Delta t$. With the aid of a software algorithm, the point in time to is determined at which the charge curve of the capacitor is near half of its maximum voltage Ucmax. In the following measurement, a clock interval $\Delta t$ is begun earlier (at the point in time tn−1) with the charging. Due to the longer charge time, a capacitor voltage Uc1 and an associated digital value result. In the following measurement, a clock interval $\Delta t$ is begun later (at the point in time tn+1) with the charging, and a charge voltage Uc2 results with the associated digital value.

The slope m of the capacitor charge curve is determined from the relation:

$$m = (Uc1 - Uc2)/2\Delta t,$$

wherein
m is the slope in V/s,
Uc1 is the voltage at the capacitor that was charged as of the point in time tn−1,
Uc2 is the voltage at the capacitor that was charged as of the point in time tn+1,
and $\Delta t$ is the clock interval.

The slope m determined in on-line operation is then used in order to determine the charge time $t_c$ as of the point in time tn+1 from the relation $$t_c = U_c/m$$

In the selected variants, the capacitor charge curve is selected so that it rises approximately linearly over at least three clock intervals Δt until it reaches its maximum value Ucmax. However, it is also possible to implement an analog calculation to determine the slope m in that only two time intervals Δt are evaluated.

The variants shown in FIGS. 4 and 5 can be combined with one another.

The propagation time $t_L$ is then determined from the relation $$t_L = t_w + n \times \Delta t + U_c/m$$

It is advantageous when a plurality of measurement results is averaged to determine the concentration of toner particles in the carrier fluid. Because the propagation time $t_L$ is in the microsecond range and the speed of change for the concentration k is small, a large number of individual values can be evaluated. For example, an averaging of 800 individual measurements can occur. The determination of the concentration k of toner particles can then occur at constant time intervals, advantageously at a time interval of 1 s. After every measurement cycle (typically 1 s), the working point can be sought again according to FIG. 4 and the slope m of the charge curve can be determined. The slope m can also be determined from a plurality of measurement values (for example 20 measurement values) in order to increase the precision. Temperature fluctuations and even component aging are compensated in this way.

Figure 6:
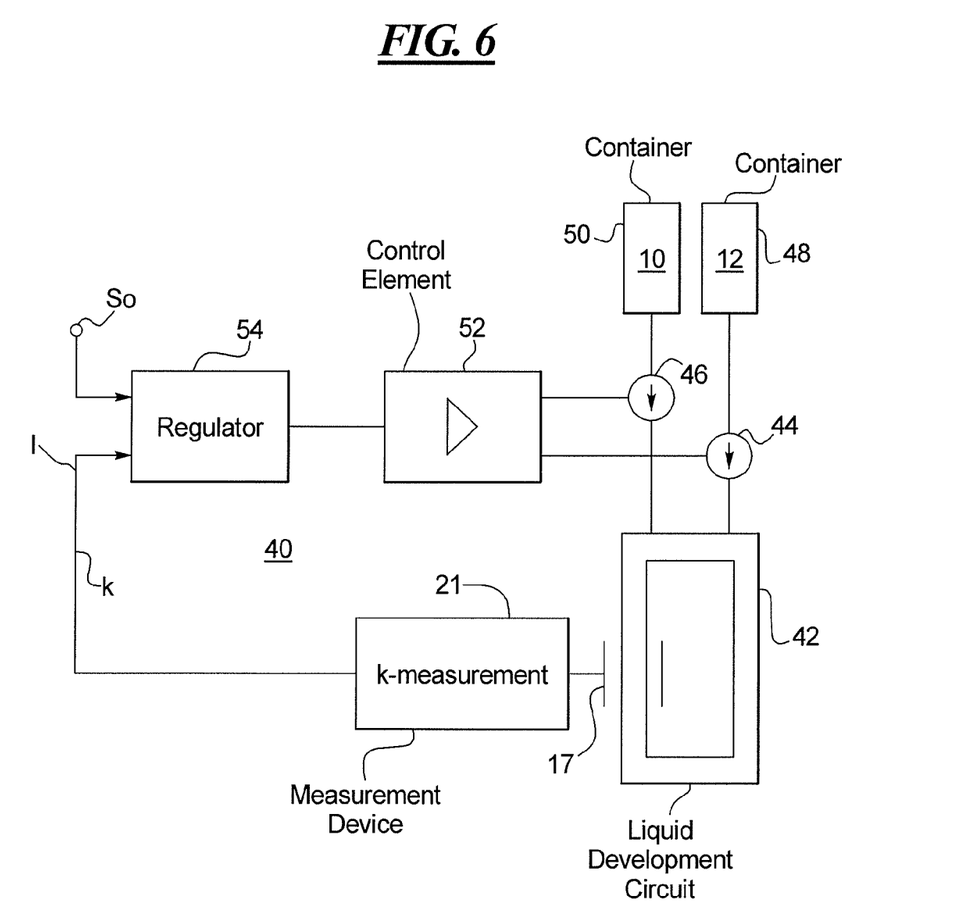
FIG. 6 is a schematic block diagram of a regulation system to regulate the concentration of toner particles in a liquid developer system for a printer or copier.

FIG. 6 shows a regulatory loop 40 for the regulation of the concentration k of toner particles in a liquid developer system for a printer or copier. The printer or copier contains a liquid developer circuit 42 (only schematically shown) with whose help latent images of an intermediate carrier are inked. The liquid developer circuit 42 can be fed via pumps 44, 46 from a container 48 with pure carrier fluid 12 or from a container 50 with a suspension of carrier fluid 10 and increased concentration of toner particles. The pumps 44, 46 are controlled via a control element 52 which is in turn controlled by a regulator 54. For the suspension located in the liquid developer circuit 42, the current concentration value k is determined with the aid of the measurement device 21 according to FIG. 2, which concentration value k is supplied as a real value I to the regulator 54. A desired value So for optimal concentration is also supplied to the regulator 54. If the regulator 54 establishes via comparison of desired value and real value that the concentration k is too low, the regulator 54 activates the control element 52 and the pump 46 so that suspension with increased toner particle concentration is supplied to the liquid developer circuit 42. The concentration k in the liquid developer circuit 42 is thereby increased so that the real value k approaches the desired value. If the regulator 54 establishes that the real value of the concentration k is higher than the desired value So (for example because carrier fluid has evaporated), the regulator 54 activates the control element 52 and the pump 44 in order to supply pure carrier fluid 12 to the liquid developer circuit 42 so that the concentration value k decreases again.

Changes in the acoustic damping of the carrier fluid lead to an increase or decrease of the signal amplitude emitted by the receiver 22. In order to keep this signal amplitude within the working range of the evaluation electronics, in a variant of the arrangement according to FIG. 2 the amplification of the receiver 22, the amplification factor of the downstream amplifier 29 and/or the amplitude of the ultrasonic signal emitted by the emitter 20 can be set or regulated to a predetermined value.

Figure 7:
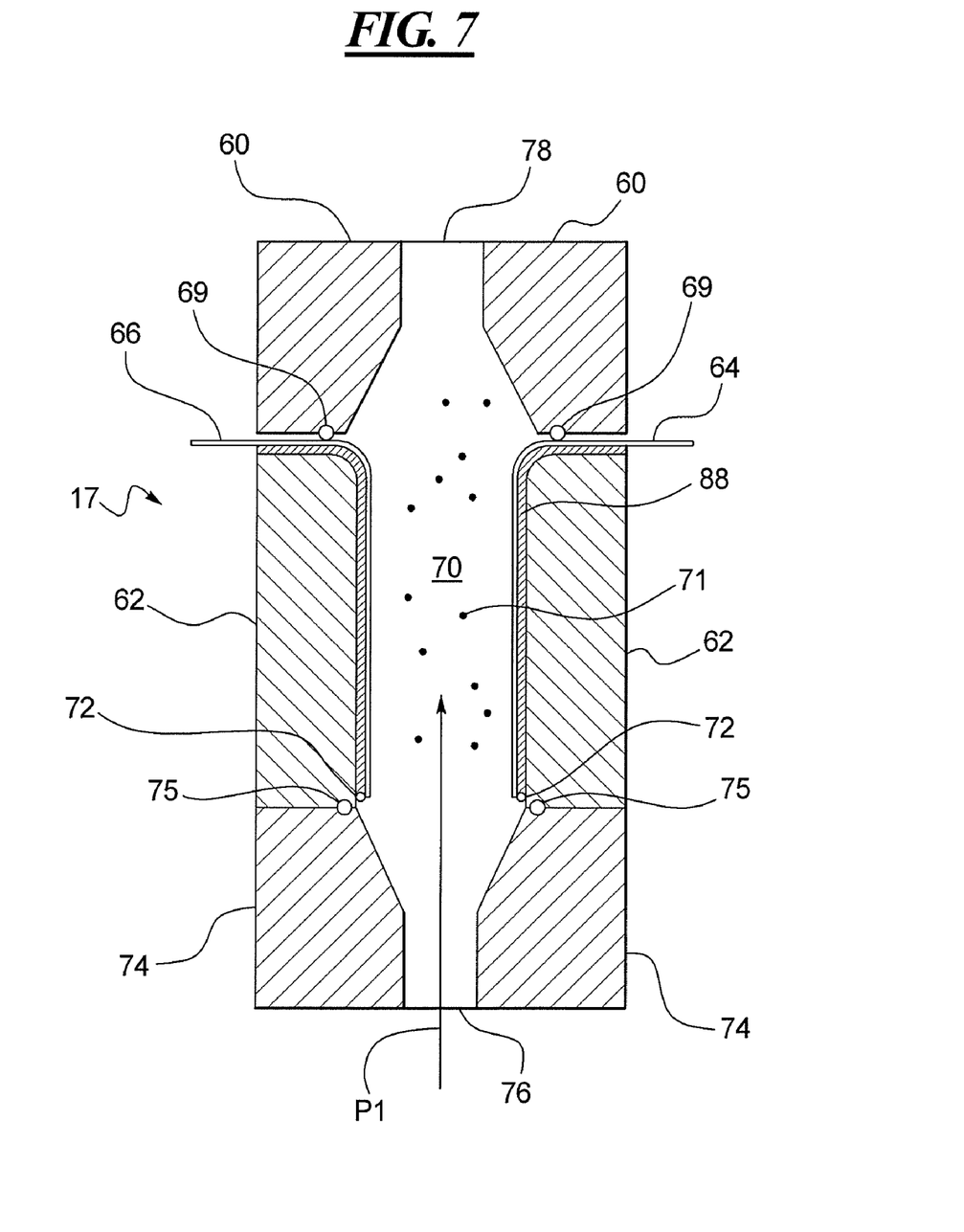
FIG. 7 is a measurement chamber to measure the concentration of the toner particles in the carrier fluid.

An important component of the complete measurement system is the measurement chamber 17, of which a principle representation is shown in FIG. 7 as a cross section. The measurement chamber 17 comprises a chamber cover 60 and, in the middle part, a film mount 62 that is executed as a separate module and bears on one side a piezo-film 64 as an ultrasonic emitter and, opposite this, a piezo-film 66 as an ultrasonic receiver. The piezo-films 64, 66 are respectively connected with the film mount 62 via an adhesive layer 68. The respective piezo-film 64, 66 is directed outward by bending along the facing side of the film mount 62. The adhesive layer 68 serves on the one hand as a connecting means to the film mount 62 and for acoustic decoupling of the piezo-films 64, 66 and the measurement chamber 17 on the other hand. Via this acoustic decoupling it is prevented that the ultrasonic signal emitted by the piezo-film 54 is transferred via the material of the measurement chamber 17 to the piezo-film 66 of the ultrasonic receiver and there causes an additional echo. The acoustic decoupling is produced via the damping of the sound signal by the adhesive layer, which amounts to at least 10 dB. The respective adhesive layer 68 is not resistant to the carrier fluid 70; therefore it is sealed against the carrier fluid 70 via a seal 72 made of plastic material at the points not covered by the respective piezo-film 64, 66. The chamber cover 60 is sealed as a separate component via a sealing ring 69 against the piezo-films 64, 66 or the facing side of the film mount 62.

The chamber floor 74, which is sealed against fluid escape via a sealing ring 75, connects to the film mount 62 as an additional separate component. The piezo-films 64, 66 are designed uniformly and are contacted outside of the measurement chamber 17. For this the piezo-films 64, 66 are curved by 90° and directed outward. In order to avoid that a projecting bulge arises at this curve due to the limited curvature radius of the piezo-material, the respective inner edge of the film mount 62 is correspondingly rounded. In an ultrasound measurement a bulge would generate a pre-echo which would adulterate the measurement value. Instead of the use of sealing rings, chamber cover 60 and chamber floor 74 can be glued with the film mount 62 to seal against fluid escape.

As mentioned, the measurement chamber 17 is used to determine the concentration of toner particles for a liquid developer system. This liquid developer system contains a suspension made up of carrier fluid 70 and toner particles 71. This suspension tends to sediment. To avoid sedimentation at the walls of the measurement chamber 17 or at the piezo-films 64, 66, which would adulterate the measurement value, the measurement chamber 17 is designed as a flow channel. For this the chamber cross section is dimensioned in the flow direction so that an average shear rate of $0.1\ s^{-1}$ or greater is achieved at the occurring flow-through speeds. Moreover, the measurement chamber 17 is arranged in operation so that its longitudinal axis is vertical, such that an infeed opening 76 in the chamber floor 74 points downward and a discharge opening 78 in the chamber cover 60 points upward. In this way both the sedimentation of toner particles and an accumulation of toner particles 71 at the piezo-films 64, 66 that will adulterate the measurement value are avoided for the developer fluids that are used.

In operation the measurement chamber 17 is actively washed by the carrier fluid 70 with the toner particles 71 in the direction of the arrow P1. Given this flow direction it is avoided that air bubbles that are possibly present can remain within the measurement chamber 17 since they are flushed out of the internal space of the measurement chamber 17 via the common direction of buoyancy of the air bubbles and flow.

A homogeneous temperature distribution is required within the measurement chamber. A singular association of speed of sound, temperature and solid material concentration is thereby ensured. This property is ensured via the use of a poorly heat-conductive material for the measurement chamber (for example Plexiglas, Makrolon (for example Makrolon 8035), fiberglass-reinforced plastic or poorly heat-conductive plastic), and its perfusion is ensured since local temperature changes of the fluid are thus minimized. The advantageous range of the heat conductivity of the material of the measurement chamber 17 is below a value of 0.5 W/(K*m).

Parameters and associated working range for the measurement chamber and the entire system are specified in the following:

| Parameter | Working range |
| --- | --- |
| Speed of sound | 800 m/s to 2000 m/s |
| Solid concentration | 0% to 50% |
| Temperature | 15° C. to 50° C. |
| Acoustic impedance of the piezo-material | $1 \times 10^6$ to $4 \times 10^6$ kg/(m$^2$s) |
| Area of emitter and receiver | 1 cm$^2$ to 4 cm$^2$ |
| Distance between emitter and receiver | 1 cm to 3 cm |

While a preferred embodiment has been illustrated and described in detail in the drawings and foregoing description, the same is to be considered as illustrative and not restrictive in character, it being understood that only the preferred embodiment has been shown and described and that all changes and modifications that come within the spirit of the invention both now or in the future are desired to be protected.

We claim as our invention:

1. A method to determine concentration of toner particles in a carrier fluid in a liquid developer system for a printer or copier, comprising the steps of:
   sending at least one ultrasonic wave through a suspension comprising the carrier fluid and the toner particles;
   determining a propagation time of the ultrasonic wave in the suspension;
   determining a concentration of the toner particles in the suspension from the propagation time;
   determining the propagation time by deriving a start signal for the emission of the ultrasonic wave from a digital clock signal of a microcomputer;
   charging a capacitor after a predetermined wait time;
   halting a charging of the capacitor as soon as a zero crossing of the ultrasonic wave that is received by the ultrasonic receiver is detected after passage of a first amplitude minimum or maximum of the ultrasonic wave;
   converting a voltage at the charged capacitor by an A/D converter whose digital value corresponds to a charge time of the capacitor; and
   calculating the propagation time from a sum of the wait time and said charge time of the capacitor.

2. A method according to claim 1 in which the wait time is derived from a quartz-controlled clock generator from the clock signal of the microcomputer and is an integer multiple of a clock interval.

3. A method according to claim 1 in which a slope of a curve of the capacitor charge is determined in an on-line operation, and is evaluated over at least two clock intervals of said digital clock signal.

4. A method according to claim 1 in which a temperature of the suspension is determined, and the concentration of the toner particles is determined from the propagation time and the temperature.

5. A method according to claim 1 in which the suspension is supplied from a liquid developer circuit of a printer or copier to a measurement chamber in which are arranged an ultrasonic emitter and an ultrasonic receiver.

6. A method according to claim 1 in which:
   a function $k=f(t_L, \theta)$ is determined in a calibration process as a characteristic line or table for different known carrier fluids with known concentration values k and known temperature values $\theta$, wherein $t_L$ is the propagation time of the sound waves in the suspension;
   the concentration value k is determined in a running operation of the printer or copier from the determined propagation time $t_L$ and the temperature value $\theta$.

7. A method according to claim 1 in which the determined concentration of toner particles is used as a real value in a regulatory loop; said real value being compared with a desired value; given a deviation between real value and the desired value, a regulator activates a control element that alters the concentration so that the real value approaches the desired value.

8. A method to determine concentration of toner particles in a carrier fluid in a liquid developer system for a printer or copier, comprising the steps of:
   sending at least one ultrasonic wave through a suspension comprising the carrier fluid in the toner particles;
   determining a propagation time of the ultrasonic wave in the suspension;
   determining a concentration of the toner particles in the suspension from the propagation time;
   determining the propagation by deriving a start signal for the emission of ultrasonic wave from a digital clock signal of a microcomputer;
   charging a capacitor after a predetermined wait time;
   halting a charging of the capacitor as soon as a zero crossing of the ultrasonic wave that is received by the ultrasonic receiver is detected after passage of a first amplitude minimum or maximum of the ultrasonic wave;
   converting a voltage at the charged capacitor by an A/D converter whose digital value corresponds to a charge time of the capacitor;
   calculating the propagation time from a sum of the wait time and said charge time of the capacitor;
   as of a passage of the wait time, the discharged capacitor is charged in a first measurement cycle at a point in time of a first of a plurality of clock pulses within a clock interval of said digital clock signal;
   if the ultrasonic receiver does not signal a receipt of an ultrasonic wave within the clock interval, the capacitor is discharged and is recharged in a further measurement cycle at a point in time of a next of the clock pulses within a following one of the clock intervals;
   providing a shifted beginning by one respective clock interval of the charging of the capacitor until the ultrasonic receiver signals receipt of an ultrasonic wave within an n-th clock interval of an n-th measurement cycle, the charging of the capacitor is thereupon halted, and the charge time is determined from the digital value of said A/D converter; and
   the propagation time is calculated from the sum of the wait time, the n-multiple of the clock interval, and the charge time.

9. A method according to claim 8 in which an absence of receipt of an ultrasonic wave within a clock interval is recognized to mean that the voltage at the capacitor exceeds a predetermined maximum value.

10. A method according to claim 8 in which a slope of a curve of the charge with which the capacitor is charged within the clock interval is set so that the charge voltage at an end of the clock interval is slightly smaller than a maximum input voltage range of the A/D converter.

* * * * *